(12) United States Patent
Ishikawa et al.

(10) Patent No.: US 7,315,043 B2
(45) Date of Patent: Jan. 1, 2008

(54) METHOD FOR FORMING AN ORGANIC SEMICONDUCTOR FILM

(75) Inventors: Takayuki Ishikawa, Kanagawa (JP);
Teigo Sakakibara, Kanagawa (JP);
Daisuke Miura, Kanagawa (JP);
Hidemitsu Uno, Matsuyama (JP);
Noboru Ono, Matsuyama (JP)

(73) Assignee: Canon Kabushiki Kaisha, Tokyo (JP)

( * ) Notice: Subject to any disclaimer, the term of this patent is extended or adjusted under 35 U.S.C. 154(b) by 0 days.

(21) Appl. No.: 11/500,996

(22) Filed: Aug. 9, 2006

(65) Prior Publication Data

US 2006/0269876 A1    Nov. 30, 2006

Related U.S. Application Data

(62) Division of application No. 11/287,257, filed on Nov. 28, 2005, now Pat. No. 7,211,120, which is a division of application No. 10/379,895, filed on Mar. 6, 2003, now Pat. No. 7,090,719.

(30) Foreign Application Priority Data

Mar. 8, 2002    (JP) ............................... 2002/063700
Feb. 25, 2003   (JP) ............................... 2003/047459

(51) Int. Cl.
*H01L 21/00* (2006.01)
*D06P 5/04* (2006.01)

(52) U.S. Cl. .................. 257/40; 252/500; 252/519; 8/478; 438/82

(58) Field of Classification Search ........... 257/40; 252/500, 519; 8/478; 438/82
See application file for complete search history.

(56) References Cited

U.S. PATENT DOCUMENTS

| | | | |
|---|---|---|---|
| 6,248,458 B1 * | 6/2001 | Yoon et al. ................. | 428/690 |
| 6,403,397 B1 | 6/2002 | Katz ........................... | 438/99 |
| 6,963,080 B2 * | 11/2005 | Afzali-Ardakani et al. ... | 257/40 |
| 2002/0127491 A1 * | 9/2002 | Weiss et al. ................. | 430/296 |
| 2003/0226996 A1 | 12/2003 | Aramaki et al. ........... | 252/62.3 |
| 2005/0258417 A1 * | 11/2005 | Minakata ..................... | 257/40 |

FOREIGN PATENT DOCUMENTS

| | | |
|---|---|---|
| EP | 1 174 432 A1 | 1/2002 |
| JP | 10-31275 A | 2/1998 |
| JP | 11-349877 A | 12/1999 |
| WO | WO 00/08103 | 2/2000 |
| WO | WO 03/016599 A1 | 2/2003 |

OTHER PUBLICATIONS

Herwig et al. (Adv. Mat. 1999, 11, p. 480).*
Ito et al. (Heterocycles, vol. 52, issue 1, 2000, p. 399).*
Gregg et al. "2,3,7,8,12,13,17,18-Octakis(β-hydroxyethyl) porphyrin (Octaethanolporphyrin) and Its Liquid Crystalline Derivatives: Synthesis and Characterization" JACS, 1989, vol. 111, pp. 3024-3029.*
H. Uno et al., "Synthesis of Conjugation-expanded Porphyrins Based on the Retro Diels-Alder-Reaction," Journal of Synthetic Organic Chemistry, Japan, vol. 60, No. 6, pp. 581-592 (2002) (English Translation).
Proceedings of the 76th Annual Meeting of the Chemical Society of Japan, Mar. 16, 1999, p. 806, 1 B1 11 (English Translation).
Noboru Ono, et al., "A New Synthesis of Pyrroles and Porphyrin fused with Aromatic Rings," J. Chem. Soc., Perkin Trans. 1, pp. 417-423 (1995).
Jerry March, "Advanced Organic Chemistry," 3rd Edition, 1985, pp. 929-930.
Michael W. Wagaman et al., "Synthesis of Substituted Bicyclo[2.2.2]octatrienes," J. Org. Chem. 1997, 62, 9076-9082.
Kwart et al., "The Reverse Diels-Alder or Retrodiene Reaction" pp. 415-447 (1967).
Papies et al., "Acceleration of the (4+2)-Cycloconversion by the Alkoxide Substitutent" Tetrahedron Letters, 2799 (1980) Grimme. Syn. Commun. 23, 1267 (1993), Y. Vallee et al.
Mass. Spectrom. Rev. 3, 85-152 (1984), F. Turecek, V. Hanus.
Ichihara, "Retro-Diels-Alder Strategy in Natural Product Synthesis," Synthesis 1987, 207-222, A. Ichihara.
Sweger et al., "Retrograde Diels-Alder Reactions," Comp. Org. Syn. 5, 551-592 (1991).
P.T. Herwig et al., "A Soluble Pentacene Precursor: Synthesis, Solid-State Conversion into Pentacene and Application in a Field-Effect Transistor," Advanced Materials, vol. 11, No. 6, pp. 480-483 (1999).
A.R. Brown et al., "Precursor Route Pentacene Metal-Insulator-Semiconductor Field-Effect Transistors," J. Appl. Phys. vol. 79(4), pp. 2136-2138 (1996).
H. Uno et al., "Synthesis of Conjugation-expanded Porphyrins Based on the Retro Diels-Alder-Reaction," Journal of Synthetic Organic Chemistry, Japan, vol. 60, No. 6, pp. 581-592 (2002).
Proceedings of the 78th Annual Meeting of the Chemical Society of Japan, Mar. 17, 2000, p. 1211, 3 G4 11.
Proceedings of the 79th Annual Meeting of the Chemical Society of Japan, Mar. 21, 2000, p. 1294, 3 H6 35.
Proceedings of the 81st Annual Meeting of the Chemical Society of Japan, Mar. 12, 2002, p. 136, 2 C 4-37.
Proceedings of the 81st Annual Meeting of the Chemical Society of Japan, Mar. 12, 2002, p. 990, 2 F9-14.
Ito et al., "A New Synthesis of Benzoporphyrins Using 4,7-Dihydro-4, 7-Ethano-2H-Isoindole as an Isoindole Equivalent," Heterocycles, vol. 52, No. 1 (2000), pp. 399-411.

* cited by examiner

*Primary Examiner*—Douglas McGinty
*Assistant Examiner*—Tri Nguyen
(74) *Attorney, Agent, or Firm*—Fitzpatrick, Cella, Harper & Scinto

(57) ABSTRACT

A method for forming an organic semiconductor film, comprising applying to a base material a bicyclo compound and inducing a retro-Diels-Alder reaction in the bicyclo compound.

5 Claims, 3 Drawing Sheets

METHOD FOR FORMING AN ORGANIC SEMICONDUCTOR FILM

The present application is a divisional of application Ser. No. 11/287,257, filed Nov. 28, 2005 now U.S. Pat. No. 7,211,120, which application is a divisional of application Ser. No. 10/379,895, filed Mar. 6, 2003 now U.S. Pat. No. 7,090,719, the entire contents of which are incorporated herein by reference.

BACKGROUND OF THE INVENTION

1. Field of the Invention

This invention relates to a compound of which molecular structure and solubility in a solvent can be changed by retro-Diels-Alder reaction and a method for producing the same. The present invention also relates to an ink for use in recording such as ink-jet recording, an ink cartridge, a recording unit, an ink-jet recording apparatus, a recording method and a recording medium. The present invention also relates to a pattern-forming method for use in, for example, production of a DNA chip and a liquid composition used in the method. The present invention also relates to a method for detecting environmental history to detect whether or not an object has undergone heating etc., and an article of which environmental history is detectable.

2. Related Background Art

A technique for controlling the solubility of a compound in a solvent according to the conditions has been strongly desired in various technical fields.

For example, in the field of ink-jet recording, it is preferable, in view of the ink stability, that the coloring material in ink is in a dissolved state, i.e., in a monomolecular state. On the other hand, in view of high quality image formation, when such an ink is once provided on a recording medium, it is preferable that the coloring material in the ink is quickly separated from the solvent so that it can be retained on the surface of the recording medium or in the vicinity thereof. So-called dye ink can satisfy the former requirement, and so-called pigment ink the latter, but it is difficult to satisfy the both at the same time. In recent years, there have been proposed various techniques for imparting characteristics of dyes to pigments by, for example, refining pigments or introducing water-dispersible functional groups onto the surface of pigments, but there is still left great room for improvement. Meanwhile, with the drastic improvement in performance of ink-jet printers, it has been proposed to use an ink-jet printer as an apparatus for producing devices having fine patterns, such as DNA chips.

SUMMARY OF THE INVENTION

As a result of intensive investigation based on the above technical background, the inventors of this invention found that it is very effective for further development of ink jet recording technology to develop a compound that maintains its solubility in a solvent when it exists in ink to give a stable ink but loses its solubility once it is provided on a recording medium to remain on the surface of the recording medium or in the vicinity thereof, more particularly, a coloring compound that can change its properties from those of a dye to those of a pigment according to the situation in the ink-jet recording process.

Accordingly, one object of this invention is to provide a novel compound of which solubility in a solvent is controllable and a method for preparing the same.

Another object of this invention is to provide an ink which permits recording of high quality and imparts to an article a function of detecting the environmental history of the object which makes it possible to know what environment the object has passed through.

Another object of this invention is to provide an ink-jet recording apparatus, and an ink cartridge and a recording unit both of which can be used in the apparatus.

Still another object of this invention is to provide a recording method and a recording medium both permitting the production of a recorded article of high quality.

Another object of this invention is to provide a liquid composition which can be used to permit recording of high quality as well as to permit imparting various functions to an article, such as an environmental history detecting function, which makes it possible to know what environment the article has passed through, and a controlling function for controlling various properties which include: for example, the fastness, density and chroma of a recorded article and the response characteristics and electric conductivity of a molecular device constructed by recording.

Another object of this invention is to provide a pattern generating method which permits accurate generation of a pattern as fine as nano meter order or pico meter order.

Still another object of this invention is to provide a method for detecting the environmental history of an article and an article which permits such detection.

The present invention provides a compound which comprises a solvent-philic group which has an affinity to a solvent and makes the compound soluble in the solvent, wherein the group is removed by retro-Diels-Alder reaction and removal of the group has the compound's solubility in the solvent lowered irreversibly.

Such a compound may have a tetraazaporphyrin skeleton.

Specifically, a compound having a tetraazaporphyrin skeleton is preferably one having a structure represented by the following formula (I) or (II):

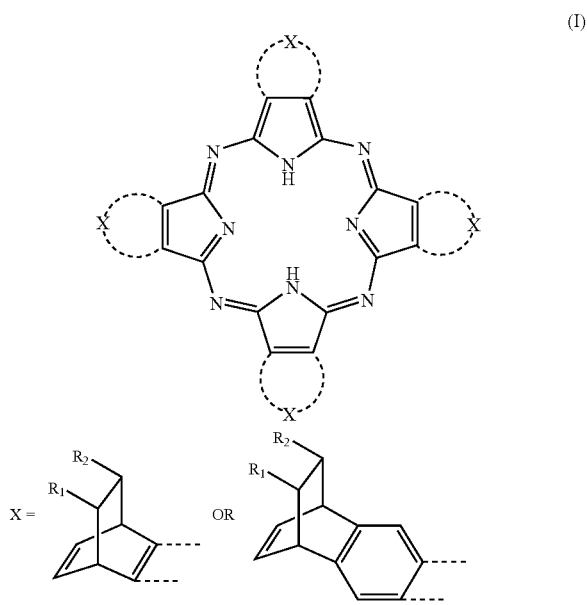

-continued (II)

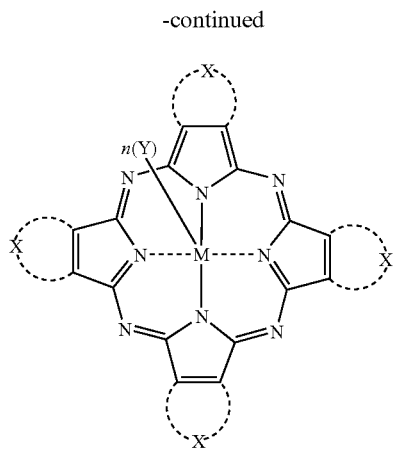

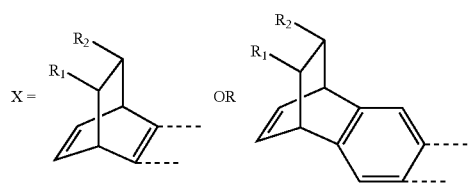

wherein $R_1$ and $R_2$ represent solvent-philic groups; M is a bi- to tetravalent coordination metal atom; Y is a halogen atom, an oxygen atom or a hydroxyl group; and n is an integer of 0 to 2.

Otherwise, such a compound may have a porphyrin skeleton.

Specifically, a compound having a porphyrin skeleton is preferably one having a structure represented by the following formula (III) or (IV):

(III)

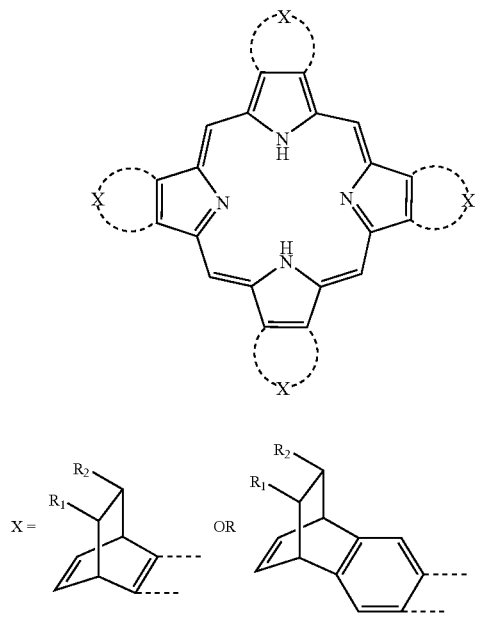

(IV)

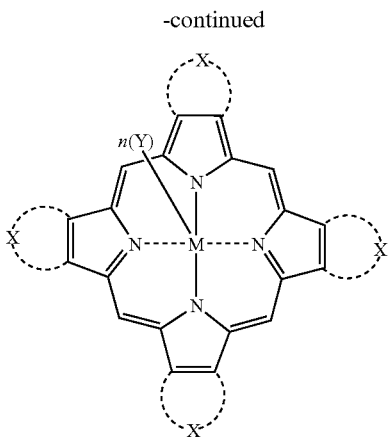

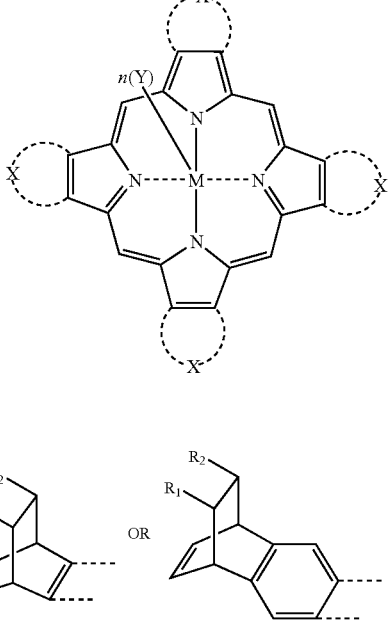

wherein $R_1$ and $R_2$ represent solvent-philic groups; M is a bi- to tetravalent coordination metal atom; Y is a halogen atom, an oxygen atom or a hydroxyl group; and n is an integer of 0 to 2.

The present invention also provides a method for synthesizing a compound having a tetraazaporphyrin skeleton that has a solvent-philic group for a solvent, where the solvent-philic group is removed by retro-Diels-Alder reaction. The method comprises the steps of:

(i) reacting a cyclohexadiene having a solvent-philic group for a solvent or a substituent group convertible into the solvent-philic group with a dicyano compound as a dienophile by Diels-Alder reaction to form a compound represented by the following formula (V), (V)

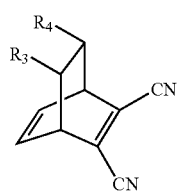

wherein $R_3$ and $R_4$ represent independently a solvent-philic group or a group convertible into a solvent-philic group, and (ii) forming a tetraazaporphyrin skeleton by subjecting the compound represented by the formula (V) to tetrameric cyclization and then coordinating a metal atom into the tetraazaporphyrin skeleton.

Further, the present invention provides a method for synthesizing a compound having a porphyrin skeleton that has a solvent-philic group for a solvent, where the solvent-philic group is removed by retro-Diels-Alder reaction. The method comprises the steps of:

(i) reacting a cyclohexadiene having a solvent-philic group for the solvent or a group convertible into the solvent-philic group as a dien with a phenylsulfonyl compound as a dienophile by Diels-Alder reaction to form at least one of a compound represented by the following formula (VI) and a compound represented by the following formula (VII),

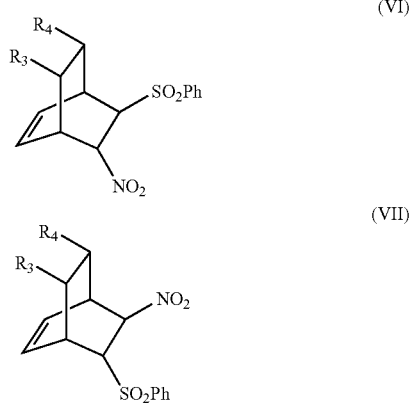

wherein $R_3$ and $R_4$ independently represent a solvent-philic group for the solvent or a group convertible into a solvent-philic group;

(ii) subjecting at least one of the compound represented by the formulas (VI) and (VII) and an isonitrile compound of the formula $CNCH_2COOR_5$ ($R_5$ represents a straight- or branched-chain alkyl group of 1 to 4 carbons) to cycloaddition reaction to form a compound represented by the following formula (VIII),

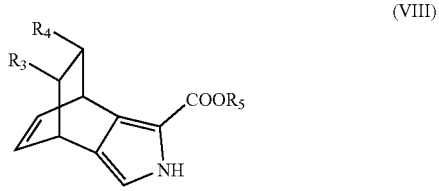

wherein $R_3$, $R_4$ and $R_5$ are as defined above; and (iii) forming a porphyrin skeleton by subjecting the compound represented by the formula (VIII) to tetrameric cyclization and then coordinating a metal atom into the porphyrin skeleton.

The present invention also provides an ink that comprises any one of the compounds and a solvent described above.

The present invention also provides an ink that comprises any one of the compounds described above and a solvent, and further comprises another compound as a coloring material.

The above ink is suitable for ink-jet printing.

The present invention also provides an ink cartridge that comprises an ink container containing the ink described above.

The present invention also provides a recording unit that comprises an ink container containing the above ink, and an ink-jet head for ejecting the ink.

Further, the present invention provides an ink-jet recording apparatus that comprises an ink container containing the above ink, and an ink-jet head for ejecting the ink.

The present invention provides a recording method that comprises the steps of:

(i) applying an ink according described above to a recording medium; and (ii) inducing retro-Diels-Alder reaction in the compound contained in the ink provided on the recording medium.

The present invention also provides a liquid composition that comprises a compound and a solvent described above. The liquid composition is suitable as a composition to be ejected in ink-jet printing.

Further, the present invention provides a method for pattern formation that comprises the steps of:

(i) applying a liquid composition according to claim 22 to a base material site-selectively; and (ii) inducing retro-Diels-Alder reaction in the compound contained in the liquid composition provided on the base material to make the compound insoluble in the solvent contained in the liquid composition.

The present invention also provides an article having on the surface thereof one of the compounds described above or a reaction product resulting from retro-Diels-Alder reaction of the compound.

The present invention also provides a method for detecting an environmental history of an article having the above-described compound on the surface thereof, the method comprises a step of detecting whether or not the compound has been subjected to retro-Diels-Alder reaction.

The present invention also provides a recording medium which comprises one of the compounds described above or a reaction product resulting from retro-Diels-Alder reaction of the compound.

DETAILED DESCRIPTION OF THE PREFERRED EMBODIMENTS

Compounds According to the Invention

Figure 1:
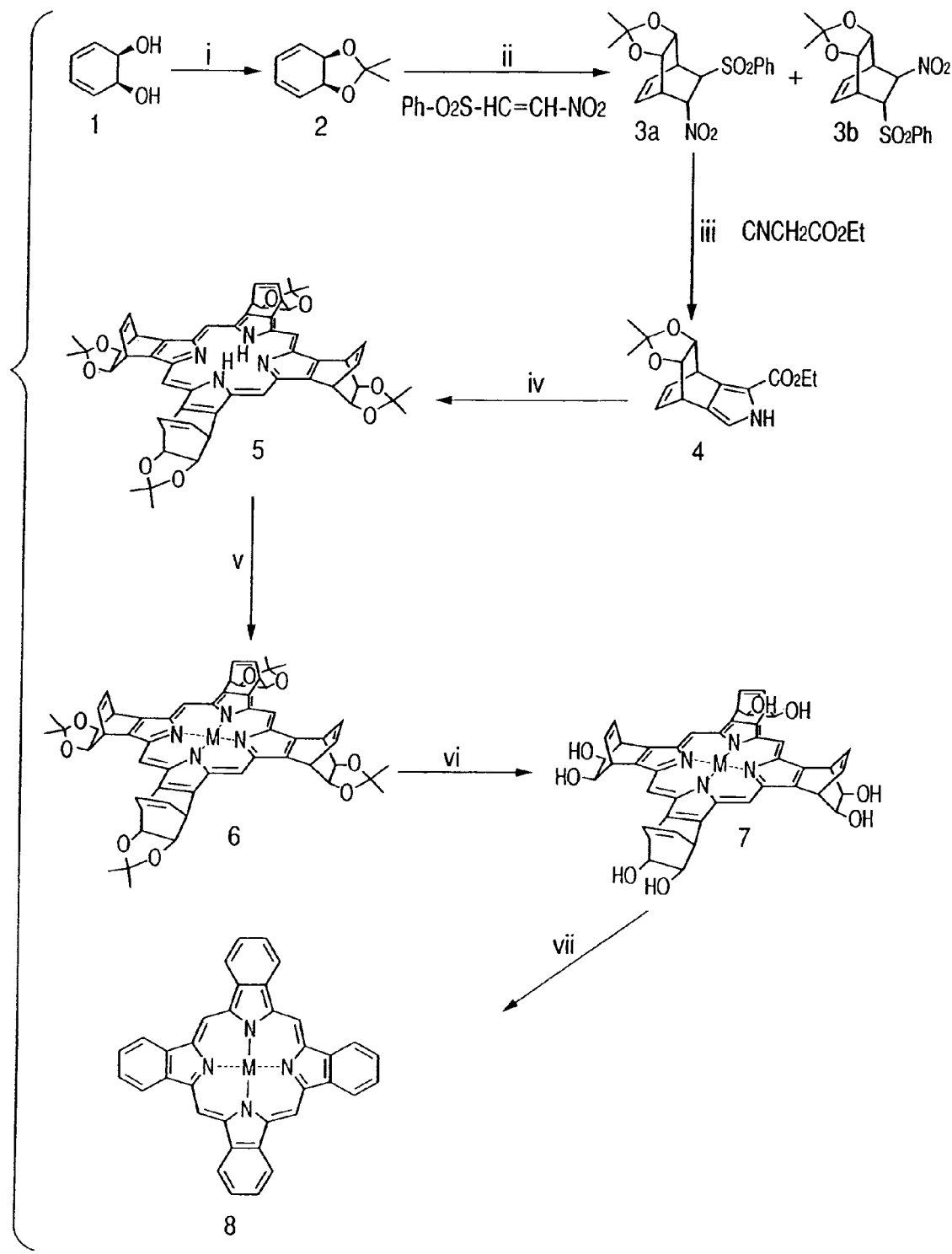
FIG. 1 is a scheme of a method for synthesizing a porphyrin compound according to this invention.

A compound according to this invention has a group having an affinity for a specified solvent (a solvent-philic group) and is soluble in the solvent, and the sovlent-phlic group is removed from the molecule by retro-Diels-Alder reaction, leading to decrease in the solubility of the compound in the solvent.

For example, when the solvent is water or a aqueous medium made of water and a hydrophilic organic solvent (e.g. alcohols, glycols and glycerols), a solvent-philic group, in this case, a hydrophilic group such as hydroxyl group, sulfonic acid group, carboxyl group and amino group, is introduced into a compound so that the solubility of the compound in water (25° C.) is at least 1% by weight. When the compound is subjected to retro-Diels-Alder reaction, the hydrophilic group is removed from the molecule of the compound to lower the solubility of the compound in the solvent as low as zero. The hydrophilic groups are not necessarily limited to those described above, such as hydroxyl group and sulfonic acid group, but may be polar substituents including at least any one of oxygen atom, nitrogen atom and sulfur atom.

When the specified solvent is an organic solvent insoluble or hardly soluble in water, a lipophilic group such as alkyl groups and alkoxy groups, preferably alkyl groups or alkoxy groups with 4 or more carbon atoms, is introduced into a compound so that the solubility of the compound in the solvent is at least 1% by weight. When the compound is subjected to retro-Diels-Alder reaction, the lipophilic group is eliminated from the molecule of the compound to lower the solubility of the compound in the water-insoluble or hardly soluble organic solvent as low as zero.

In the following, the compounds according to this invention will be described in further detail with examples.

Examples of a compound of which solubility in a solvent can be effectively controlled by eliminating the solvent-philic group by retro-Diels-Alder reaction as described above include tetraazaporphyrin compounds represented by the following formula (I) or (II) and porphyrin compounds represented by the following formula (III) or (IV).

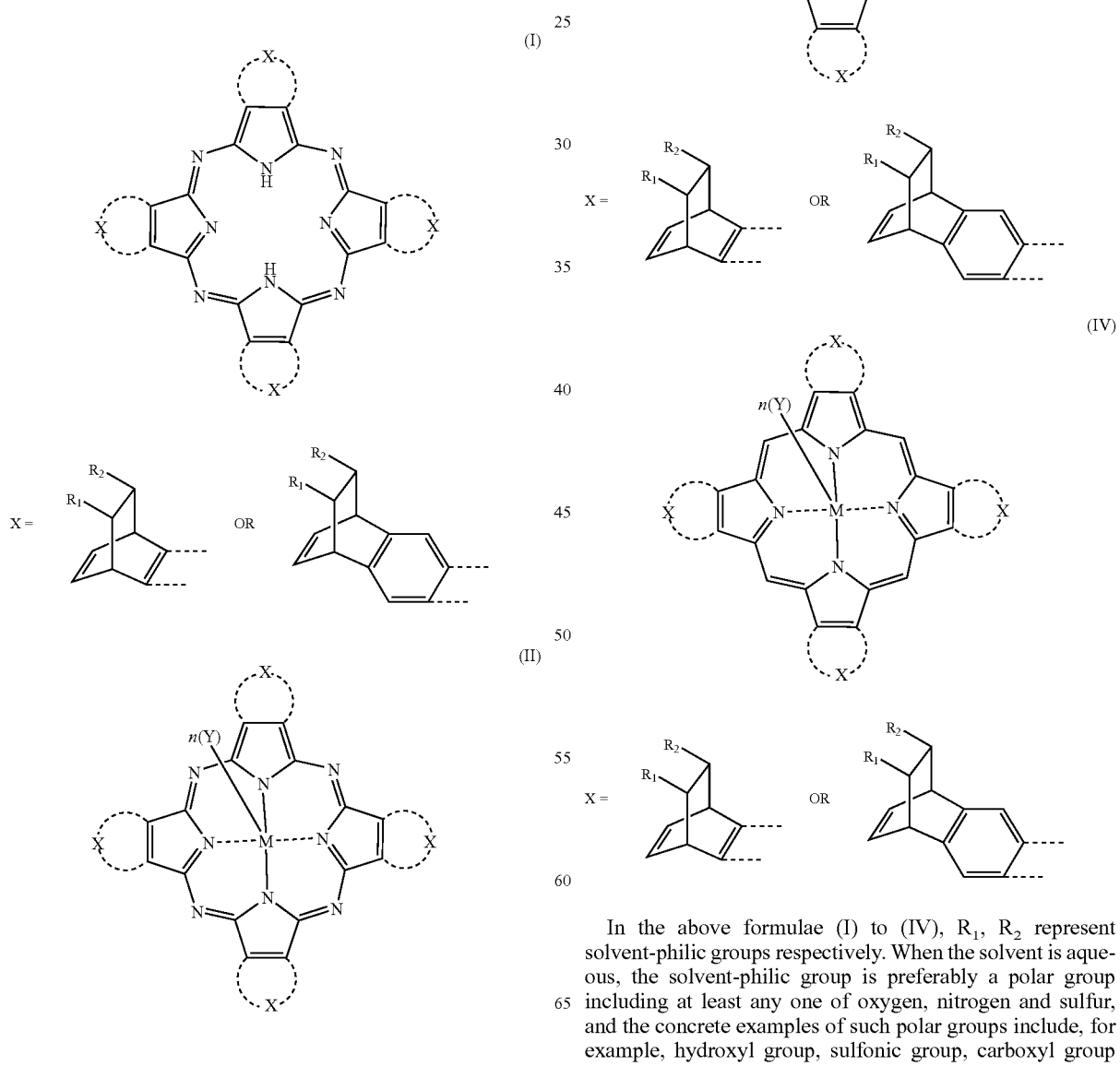

In the above formulae (I) to (IV), $R_1$, $R_2$ represent solvent-philic groups respectively. When the solvent is aqueous, the solvent-philic group is preferably a polar group including at least any one of oxygen, nitrogen and sulfur, and the concrete examples of such polar groups include, for example, hydroxyl group, sulfonic group, carboxyl group and amino group, among which hydroxyl group is more preferable. When the solvent is an organic solvent insoluble or hardly soluble in water, the solvent-philic group is preferably a lipophilic group including, for example, alkyl groups such as methyl group, ethyl group, propyl group and butyl group and alkoxy groups such as methoxy group, ethoxy group and propoxy group, among which alkyl groups or alkoxy groups with 4 or more carbon atoms are more preferable.

In the above formulae, M represents a divalent to tetravalent coordination metal such as Zn, Cu, Fe, Mg, Al, Ga, Ti or Sn; Y is one selected from halogen atoms such as chlorine, bromine and iodine, oxygen atom and hydroxyl group; and n is an integer of 0 to 2.

Compounds Having Porphyrin Skeleton with Water-Soluble Groups)

Next, described are concrete examples of porphyrin compounds of the above formula (IV) of which solubility in water can be changed.

A porphyrin compound represented by the following structural formula (IX) has hydroxyl groups as a hydrophilic group and is soluble in an aqueous solvent due to the hydroxyl groups with a solubility in water at 25° C. of 1 wt % or higher. When the hydroxyl groups are eliminated from the molecules of the compound by retro-Diels-Alder reaction, the solubility of the compound in the aqueous solvent is lowered.

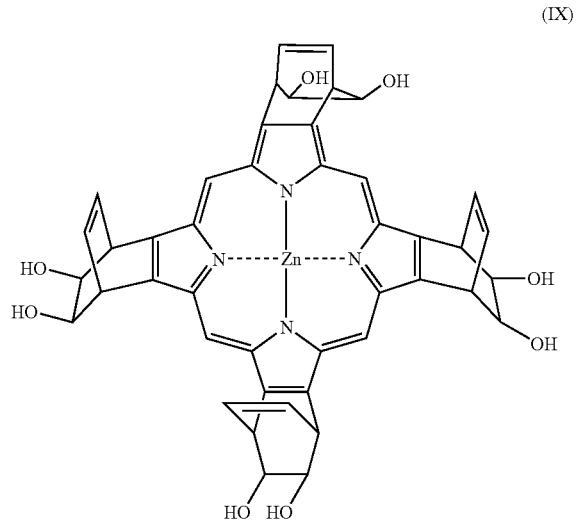

(IX)

In general, porphyrin compounds are hardly insoluble in solvents, for example, solubility in water at 25° C. of less than 1 wt %, because of high flatness of porphyrin skeleton portion and π-π stacking. However, the porphyrin compound having the above formula (IX), where bicyclo[2,2,2] octadiene skeletons with hydroxyl groups are condensed, is soluble in aqueous solvents due to the presence of bulky bicyclo[2,2,2]octadiene skeleton and hydroxyl groups. When the compound of the above formula (IX) is subjected to retro-Diels-Alder reaction so as to eliminate the bridging ethylene moieties in the molecule, the combined effect of the removal of hydroxy groups and stacking of the molecules due to the bulk reduction of the bicyclo[2,2,2]octadiene skeleton lowers the solubility in aqueous solvents, and the compound becomes insoluble or almost insoluble in, for example, water at 25° C. The above porphyrin compound represented by the formula (IX) is an example of the compounds of the formula (IV) of this invention, where the central metal is zinc and the solvent-philic groups are hydroxyl groups, but the compounds of this invention are not limited to the above example, and they may be appropriately selected from other porphyrin compounds, considering polarity in view of the solvent for which the compounds should have affinity. As for the central metal, not only zinc but also copper, magnesium or aluminium may be selected properly so as to control the required electron state or the factors resulting from the structure (e.g. absorption spectrum) of the compound, taking into consideration of ease of synthesis. Substituents convertible into solvent-philic groups are not specifically limited, but in view of easy synthesis, hydroxyl group can be modified into ether or ester to attach various substituents such as long-chain alkyl and ethylene glycol groups.

Method for Synthesizing Porphyrin Compounds

In the following the method for synthesizing a porphyrin compound according to this invention will be described.

The compound according to this invention, which has a porphyrin skeleton and solvent-philic groups for a specified solvent and of which solvent-philic groups are eliminable by retro-Diels-Alder reaction, can be synthesized in the following steps of:

(i) reacting a cyclohexadiene having a solvent-philic group or a substituent group convertible to a solvent-philic group (a dien compound) and a phenyl sulfonyl compound (a dienophile) by Diels-Alder reaction to obtain at least one of the compounds of formulas (VI) and (VII):

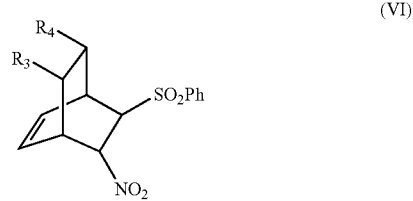

(VI)

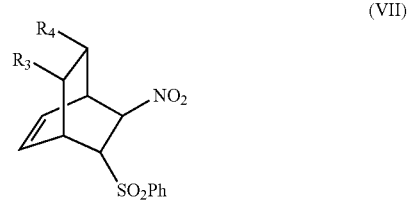

(VII)

wherein $R_3$ and $R_4$ represent independently a solvent-philic group for the specified solvent or a group convertible to a solvent-philic group;

(ii) subjecting at least one of the compounds of formulas (VI) and (VII) and an isonitrile compound having the formula $CNCH_2COOR_5$ ($R_5$ represents a straight- or branched-chain alkyl group with 1 to 4 carbon atoms) to cycloaddition reaction to obtain the compound having the following formula (VIII):

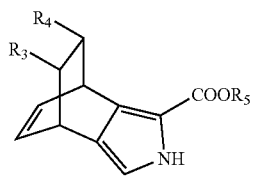

(VIII)

wherein $R_5$ represents a straight- or branched-chain alkyl group with 1 to 4 carbon atoms; and (iii) subjecting the compound represented by the above formula (VIII) to tetrameric cyclization to form a porphyrin skeleton and then coordinating a metal atom to the porphyrin skeleton. In the above formulae (VI) and (VII), $R_3$ and $R_4$ may be the same as $R_1$ and $R_2$ in the above formulae (I) to (IV), or may be groups convertible to $R_1$ and $R_2$. The groups convertible to solvent-philic groups include, for example, $R_1$ or $R_2$ protected with a protecting group so as to prevent the reaction of $R_1$ or $R_2$ or both during the synthesis process of porphyrin skeleton.

Now a synthesis method for the porphyrin compound of the above formula (IX) will be described in more detail. The compound can be synthesized by the method shown in the scheme of FIG. 1. In FIG. 1, reference numerals attached to the chemical formulae are to denote compounds of the formulae and small roman numerals attached to the arrows are to denote synthesis steps.

First, 3,5-cyclohexadiene-1,2-diol is reacted in the presence of acetone, dimethoxypropane and p-toluenesulfonic acid to obtain a compound 2 of which hydroxyl groups are protected (step i). The compound 2 and 2-nitro-1-phenylsulfonylethylene, as a dienophile, are subjected to Diels-Alder reaction in the presence of toluene to obtain compounds 3a and 3b (step ii) The resultant compounds 3a and 3b are dissolved in dry THF (tetrahydrofuran) under nitrogen atmosphere, dry ethyl isocyanoacetate is added on the ice bath, and dry 1,8-diazabicyclo-[5,4,0]undecene-7 (hereinafter referred to as "DBU") is added and reacted by modified Barton-Zard reaction method to obtain a compound 4 as a precursor of the porphyrin compound (step iii).

The modified Barton-Zard reaction method used herein is a method for constructing a wider variety of aromatic rings, which has been established by improving a method for constructing a pyrrole skeleton from nitroalkene, an aromatic nitro compound and ethyl isocyanoacetate, as disclosed in J. Chem. Soc. Perkin Trans. 1, 1996, 417, by N. Ono, H. Hironaga, K. Ono, S. Kaneko, T. Murashima, T. Ueda, C. Tsukamura and T. Ogawa. The inventors used this reaction in combination with Diels-Alder reaction and successfully synthesized compounds having a novel function, which led to the completion of this invention. The Barton-Zard method has been known as a method for constructing an alkyl-substituted pyrrole skeleton. In this invention, however, the Barton-Zard method was modified to construct an aromatic-ring-substituted pigment precursor (aryl-substituted pigment precursor) of pyrrole skeleton. Specifically, the modified Barton-Zard method is used in the last step in the process of constructing a pyrrole ring where a sulfonyl compound or a nitrosulfoyl compound having substituted solvent-philic groups is synthesized as a starting material through Diels-Alder reaction, and then reacted with ethyl isocyanoacetate.

The compound 4 is dissolved in dry THF in a nitrogen atmosphere, and aluminium lithium hydride is added and reacted while icing the mixture to obtain a compound 5 which is a tetramer of the compound 4 having a porphyrin skeleton (step iv). The compound together with a metal salt, such as zinc acetate, is dissolved in, for example, chloroform-methanol and reacted so that the metal is coordinately bonded to the porphyrin skeleton to obtain a compound 6 (step v). Then, the hydroxyl groups of the compound 6 is deprotected to give a compound 7 having the above formula (IX) (step vi). The solubility of the resultant compound 7 at 25° C. is about 1.4 g in 1 g of methanol, about 2.55 g in 1 g of isopropyl alcohol, and about 0.8 g in 1 g of a mixed solvent of water/isopropyl alcohol.

The compound 8 obtained by subjecting the compound 7 to retro-Diels-Alder reaction to remove hydroxyl groups therefrom is almost insoluble in a aqueous solvent at 25° C.

(Diels-Alder Reaction and Retro-Diels-Alder Reaction)

Diels-Alder reaction is a reaction in which a compound having a double bond or a triple bond is addition-bonded to the first and forth positions of a conjugated double bonds to produce a six-membered hydroaromatic ring. Retro-Diels-Alder reaction is a reverse reaction of Diels-Alder reaction. For example, retro-Diels-Alder reaction of a compound having a fused ring portion of a bicyclo[2,2,2]octadiene skeleton removes ethylene at the bridging portion of the compound. Thus, the solubility of the compound can be controlled if the ethylene portion bears a group(s) that endow increased solubility in a solvent. If removal of the ethylene portion by retro-Deals-Alder reaction according to the present invention leads to formation of a π conjugated system, it is preferable to design the original compound as such that the bulky structure becomes flat as a result of the π conjugated system construction, since such a molecular structure enables control of the agglomeration and association properties of the compound resulting from retro-Diels-Alder reaction.

In order to realize the above preferred embodiment, it is preferable to deign such a system that the interaction between molecules increases after retro-Diels-Alder reaction due to hydrogen bond, van der Waals force, electrostatic force, polarity etc. Thus, even in a system where the association of a compound is too large to control in the prior art, if the properties of the compound before and after the retro-Diels-Alder reaction are properly designed, its agglomeration or association properties can be controlled effectively.

In the compounds of this invention, the substituents introduced at the bridging portion and removed by the retro-Diels-Alder reaction can be highly stable and safe. In other words, the reaction system can be designed so as not to cause a reversible or secondary reaction. It is generally known that Diels-Alder reaction between a diene compound and a dienophile compound is a reversible reaction where an exothermic reaction (Diels-Alder reaction) and an endothermic reaction (retro-Diels-Alder reaction) are in an equilibrium state. Japanese Patent Application Laid-Open No.

11-349877 discloses an example of taking advantage of this point to control the viscosity/temperature of an ink-jet ink carrier. Since the reaction used in the above invention is a reversible reaction, if the above reaction is applied to the present invention, cooling of a compound to decrease solubility may induce cyclization reaction again, causing increase in solubility of the compound. Further, in the above invention, the diene compound and dienophile compound present after retro-Diels-Alder reaction are unstable, so that oxidation reaction may occur as a secondary reaction. Thus, the above invention is not suitable for the purpose of this invention. Japanese Patent Application Laid-Open No. 10-31275 discloses control of polarity (solubility, cohesiveness) by using the decomposition reaction of a triallylmethane compound by UV/heat application or by using a photo/thermo reversible compounds such as a photochromic compound. Since the polarity-controlling portion used in the above invention is a system that is decomposed by radical ionic cleavage so that an irreversible state can be achieved. However, the by-products of the reaction are instable and liable to induce an oxidation deterioration reaction, which may cause adverse effects. Further, since the photochromic reaction is a reversible reaction induced by visible-/ultraviolet rays or heat, it is difficult to keep a certain state stably, so that it is not suitable for the purpose of the present invention.

Accordingly, in this invention, the reaction system is preferably designed as such that the products from a precursor by the retro-Diels-Alder reaction are not in a relationship of a diene and a dienophile, between which Diels-Alder reaction may not occur. In one embodiment of this invention, the compound removed by the retro-Diels-Alder reaction (1,2-ethylenediol) will not become a dienophile. Further, 1,2-ethylenediol itself is an unstable compound and will be oxidized to hydroxyacetaldehyde, so that no compounds that react with the water-insoluble compound 8 is present in the system, which has been made water-insoluble. As a result, the retro-Diels-Alder reaction progresses irreversibly. As described above, in order to allow retro-Diels-Alder reaction to progress irreversibly, it is preferable to design the reaction system as such that the compound eliminated by retro-Diels-Alder reaction is converted, by oxidation, reduction or isomerization, into a compound which has no reactive double bond with which retro-Diels-Alder reaction will not occur.

Method for Retro-Diels-Alder Reaction

One way to cause retro-Diels-Alder reaction in a compound of this invention, e.g., the compound 7 in the scheme of FIG. 1, is to apply energy by means of heating, irradiation of light, electromagnetic wave or radiation.

Compound Having Tetraazaporphyrin Skeleton with Hydrophilic Groups

Another example of the compounds of this invention is a tetraazaporphyrin compound having the following structural formula (X).

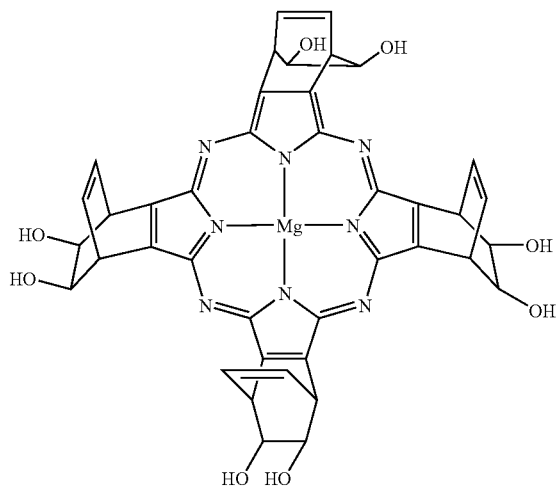

The above compound maintains its solubility in aqueous solvents due to the hydroxyl groups bonded to its bicyclo [2,2,2]octadiene skeleton and loses its good solubility in aqueouse solvents when ethylenediol is split from the molecule by retro-Diels-Alder reaction, in the same manner as with the compound of formula (IX).

Method for Synthesizing Tetraazaporphyrin Compounds

The method for synthesizing tetraazaporphyrin compounds of this invention will be described.

Compounds of this invention having a tetraazaporphyrin skeleton with solvent-philic groups removable by retro-Diels-Alder reaction compounds can be synthesized in the steps of:

(i) by reacting cyclohexadiene having solvent-philic groups or substituents convertible into the solvent-philic groups and a dicyano compound as a dienophile, by Diels-Alder reaction to obtain a compound having the following formula (V):

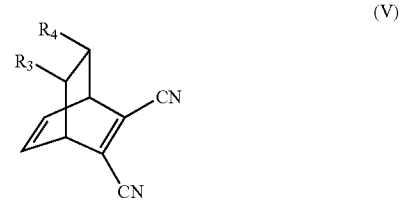

wherein $R_3$ and $R_4$ independently represent solvent-philic groups or groups convertible to the solvent-philic groups; and (ii) forming a tetraazaporphyrin skeleton by tetrameric cyclization of the compound of formula (V) and then coordinately bonding a metal atom to the tetraazaporphyrin skeleton. In the above formula, $R_3$ and $R_4$ represent the same groups as $R_1$ and $R_2$ in the above formulae (I) to (IV), or groups convertible into these groups, for example, $R_1$ and $R_2$ protected with a protecting group so as to prevent the reaction of these groups during the synthesis process of the porphyrin compound.

Now the method for synthesizing the tetraazaporphyrin compound having the above formula (X) will be described in further detail. This compound can be synthesized by the method shown in the scheme of FIG. 2. First, 3,5-cyclohexadien-1,2-diol is reacted in the presence of acetone, dimethoxypropane and p-toluenesulfonic acid to obtain a compound 2' of which hydroxyl groups are protected (step i'). The compound 2' and dicyanoacetylene are reacted for Diels-Alder reaction in the presence of toluene to obtain a dicyano compound 31 (step ii'). The resultant compound 3' and di-n-butoxymagnesium are dissolved in, for example, n-butanol under a nitrogen atmosphere and reacted to form a tetramer, that is, a tetraazaporphyrin skeleton while coordinately bonding the metal element to the tetraazaporphyrin skeleton, to obtain a compound 4' (step iii'). Then the compound 4' is subjected to deprotection of hydroxyl groups to obtain a compound 5' having the above formula (X) (step iv'). The solubility of the resultant compound 5' in water at 25° C. is about 50% by weight.

As shown in the step v', a compound 6' not having hydroxyl groups obtained from the compound 5' by retro-Diels-Alder reaction is insoluble (zero solubility) in water at 25° C.

Compounds with Oil-Philic Groups

While this invention has been described in terms of the compounds excellent in solubility in aqueous medium, it should be understood that the technique of this invention is not limited thereto, but it is possible to lower solubility of an oil-soluble compound in hydrophobic solvents by retro-Diels-Alder reaction. The examples of such compounds include, for example, compounds having a structure represented by the following formula (XI). These compounds can be easily obtained by modifying the hydroxyl groups of the above-described compounds with hydrophobic groups such as alkyl group or by using a proper starting material for synthesis.

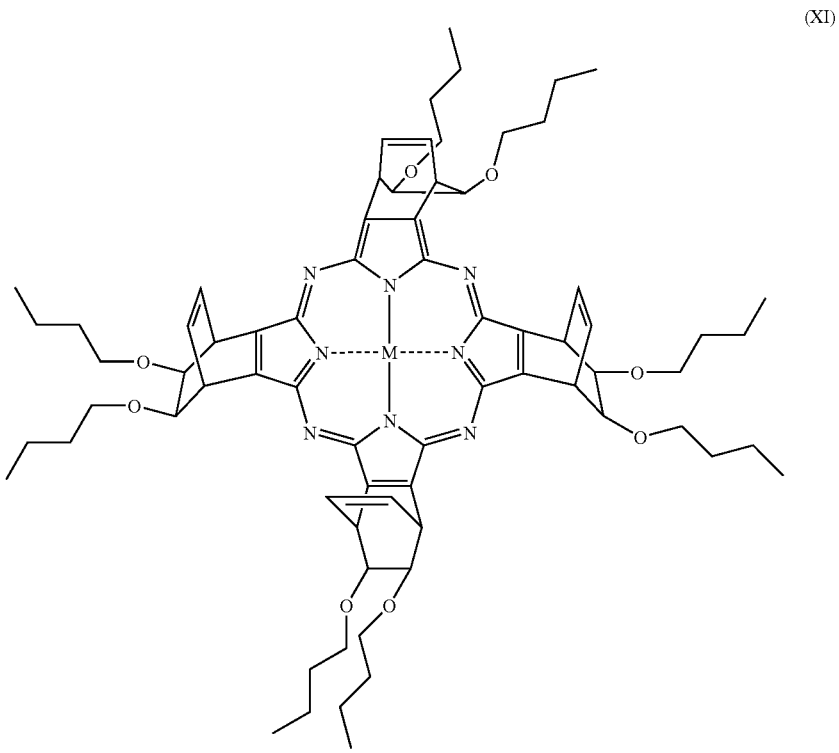

(XI)

Applications of Novel Compounds of the Invention

In the following a variety of applications of the above-described compounds will be described.

Ink

Since solubility of the compounds of the invention can be controlled as described above, they can be used in ink to achieve high quality printing. Specifically, when a compound of the invention is used in an ink as a coloring material, it is possible to change a dye-type coloring material to a pigment-type coloring material. More specifically, if the compound present in an ink in a dissolved state is applied on a recording medium and then subjected to retro-Diels-Alder reaction, the solubility is lowered and the separation of the coloring material from the solvent occurs rapidly on the recording medium. According to the technique of this invention, if the compound (coloring material) resulting from retro-Diels-Alder reaction has a structure excellent in fastness (including light fastness and gas fastness), both the superior points of dye ink and pigment ink can be enjoyed. The coloring material that can be contained in the ink composition of of this invention is not specifically limited but use of those having a strong associated state with low solubility and dispersibility is very effective and thus preferable. The suitable coloring materials include, for example, polycyclic coloring materials such as azo coloring materials, quinone dyes, quinacridon pigments; various chelate coloring materials; nitro coloring materials; nitroso coloring materials; and aniline black. These coloring materials are considered to have strong molecular interaction with low solubility and dispersibility.

To be a compound (coloring material) excellent in durability (fastness), the compound must have such a structure that the molecular interaction allows the compound not affected by external deterioration factors (light, gas). Thus it is important to control the molecular interaction.

Ink-Jet Ink

An aqueous ink-jet ink can be obtained by using a water-soluble compound of this invention, which is represented by the above formula (IX) or (X), as a coloring material.

The solvents used-for aqueous ink include, for example, water, and a mixture of water and a water-soluble organic solvent. When a mixture of water and a water-soluble organic solvent is used, preferably the content of the water-soluble organic solvent is, not limited to, in the range of 3 to 50% by mass of the total mass of the ink. And preferably the content of the water in ink is in the range of 50 to 95% by mass of the total mass of the ink.

The water-soluble organic solvents applicable include: for example, alkyl alcohols with 1 to 5 carbons, such as methyl alcohol, ethyl alcohol, n-propyl alcohol, isopropyl alcohol, n-butyl alcohol, sec-butyl alcohol, tert-butyl alcohol, isobutylalcohol and n-pentanol; amides, such as dimethylformamide and dimethylacetamide; ketones or ketoalcohols, such as acetone and diacetone alcohol; ethers, such as tetrahydrofuran and dioxane; oxyethylene or oxypropylene copolymers, such as diethylene glycol, triethylene glycol, tetraethylene glycol, dipropylene glycol, tripropylene glycol, polyethylene glycol and polypropylene glycol; alkylene glycols whose alkylene groups have 2 to 6 carbons, such as ethylene glycol, propylene glycol, trimethylene glycol, triethylene glycol and 1,2,6-hexanetriol; glycerol; lower alkyl ethers, such as ethylene glycol monomethyl (or ethyl) ether, diethylene glycol monomethyl (or ethyl) ether and triethylene glycol monomethyl (or ethyl) ether; lower alkyl ethers of polyhydric alcohol, such as triethylene glycol dimethyl (or ethyl) ether and tetraethylene glycol dimethyl (or ethyl) ether; alkanolamines, such as monoethanolamine, diethanolamine and triethanolamine; sulfolane; N-methyl-2-pyrrolidone; 2-pyrrolidone; and 1,3-dimethyl-2-imidazolidinone. These water-soluble organic solvents can be used alone or as a mixture. Further, in order for the aqueous ink of this invention (ink whose solvent is aqueous solvent) to have desired physical properties, in addition to the above described ingredients, additives such as viscosity modifier, antifoamer, antiseptic agent, mildewproofing agent, surfactant and antioxidant can be added depending on the situation.

Another Embodiment of Ink

While in the above-described inks, the compound of the present invention is used as a coloring material, in the ink according to this invention, the compound of which solubility in the ink solvent is lowered by retro-Diels-Alder reaction is not necessary a coloring material. For example, the compound according to this invention can also be used as at least one of the components of the ink. For example, when a compound of the invention of which solubility is changed by retro-Diels-Alder reaction is contained in the ink as a water soluble binder polymer, the polymer that exists in a dissolved state in the ink becomes insoluble in water by retro-Diels-Alder reaction after the ink was applied to the recording medium to give a recorded article of good water resistance, Ink-Jet Recording Method The aqueous ink containing a porphyrin compound having the above formula (IX) or a tetraazaporphyrin compound having the above formula (X) can be suitably used for ink-jet recording. Specifically, ink-jet recording using such an aqueous ink is performed in the steps of: for example, filling an ink tank of a commercially available on-demand type ink-jet printer (e.g. BJ-F900 (trade name), manufactured by Canon) with the ink; mounting the ink tank on the printer and providing the ink onto a recording medium; and applying energy to the ink on the recording medium to cause retro-Diels-Alder reaction. As the energy applied to the ink, heat, light, etc. can be used as already described. Preferred timing of application of ink onto the recording medium and energy application to the ink is, with a recording medium of good water permeability, is that energy is applied before the ink is fully absorbed in the recording medium; in more particular, when the recording medium is plain paper (PB paper manufactured by Canon) of good water permeability, the time lag between ink application and energy application is about 1 second or less. Accordingly, in the ink-jet recording apparatus used for such recording, energy providing means may be provided very close to the recording head or next to the recording head so that providing ink on the recording medium and applying energy to the ink can be performed almost at the same time or with a time lag as short as possible.

Ink-Jet Recording Apparatus

A recording apparatus of this invention which includes a pre-heater and a halogen heater as means for causing retro-Diels-Alder reaction will be described with reference to FIG. 3.

Figure 3:
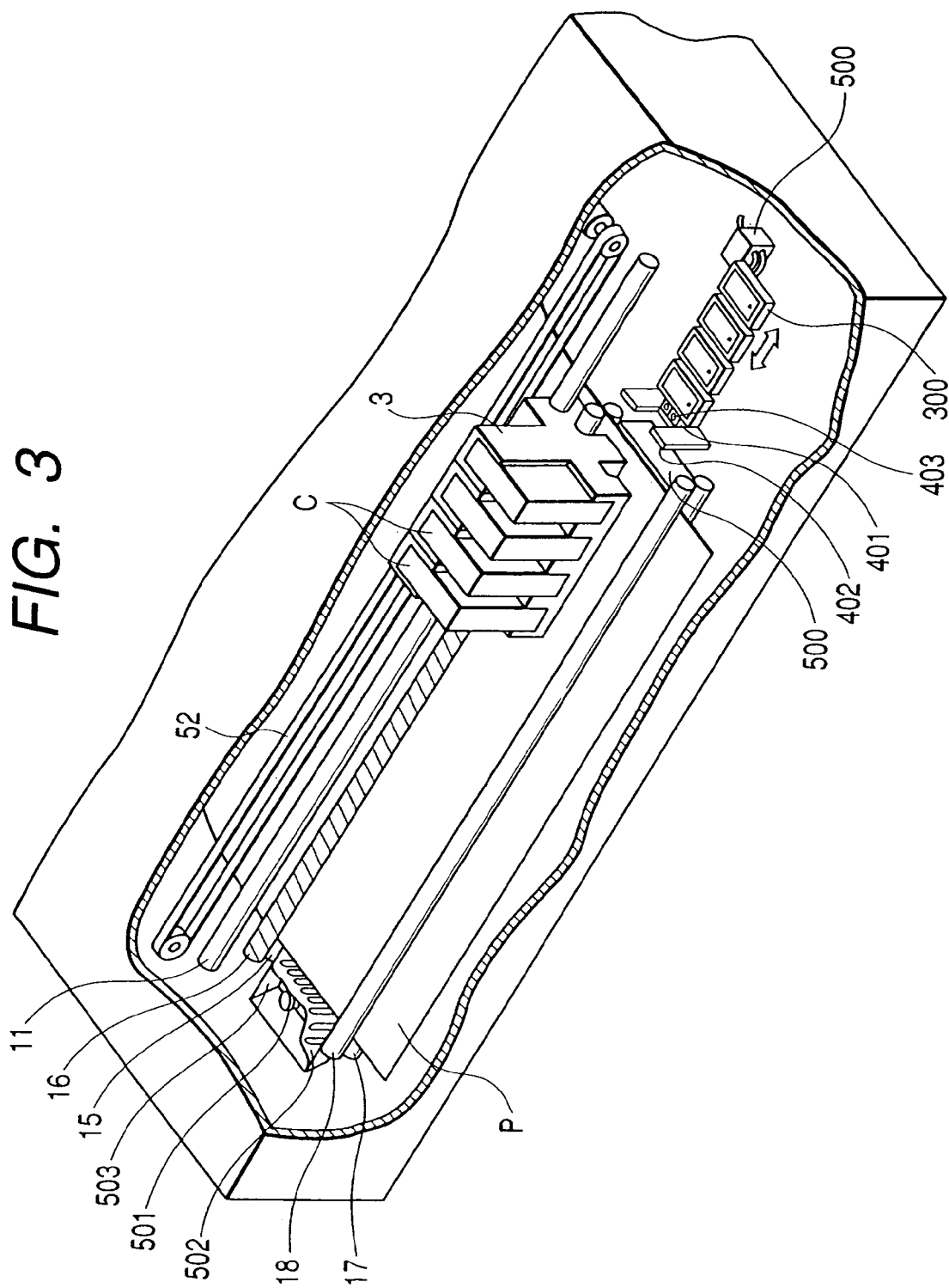
FIG. 3 is a schematic perspective view of an ink-jet printer according to this invention.

FIG. 3 is a schematic perspective view of a full-color serial-type printer comprising a changeable recording head (not shown in the figure), and ink tanks C removably attached to the above recording head. The ink tanks C are one form of an ink container which contains the ink of this invention. The recording head and the ink tanks C are attached to a carriage 3 in a detachable manner. The carriage 3 engages with a guide shaft 11 in its sliding direction along the shaft and is connected to part of a driving belt 52 which is moved by a main scanning motor (not shown in the figure). This permits scanning by the recording head and ink tanks in the direction along the guide shaft. There exist conveyer rollers 16 extending almost parallel to the guide shaft in the back of and in front of the recording area where recording is performed by the scanning recording head and ink cartridge. The conveyer rollers 16 which also serve as a pre-heater, are driven by a control circuit and a subscanning motor (neither is shown in the figure) to heat the recording medium P and the novel compound of this invention contained in the ink provided on the recording medium to induce retro-Diels-Alder reaction, while conveying the recording medium P. The recording medium P being conveyed is subjected to main heating from the back of the printed portion at a platen part by a infrared heating heater unit 500 so that the recording medium P and the novel compound of this invention can be heated to a desired temperature to allow retro-Diels-Alder reaction to progress rapidly. The infrared heater unit 500 comprises: for example, a halogen heater 501; a net form platen 502 that prevents ingression of the recording medium and allows efficient heating; a reflecting plate for converging infrared light on the recording medium (not shown in the figure); a sensor for sensing temperature changes (thermistor) (not shown in the figure); and a circuit for controlling the above sensor (not shown in the figure). While the heating means of the above ink-jet recording apparatus was explained as infrared heating by using a halogen heater, the heating means can be another retro-Diels-Alder reaction inducing means, such as hot-air heating system and semiconductor laser for photo-dissociation, depending on the retro-Diels-Alder reaction properties of the novel compound of this invention.

Recording Unit

The recording unit according to this invention includes a recording head, an ink cartridge (ink container), a carriage device and a paper conveyance device, which are required for an ink-jet recording apparatus, and in addition, an external energy providing device (e.g. a heating device, a light irradiating device or an electromagnetic wave irradiating device). A controller for sequentially controlling these devices and devices for ink recovering system are appropriately selected and installed.

Ink Cartridge

The ink cartridge according to this invention is one selected from the ink cartridges used in a common ink-jet recording system. Such ink cartridges include, for example, the following types: a type mounted on the upper portion of a recording head so that ink can be fed to the head; another type having a tube through which ink is fed to a recording head; and still another type integrated into a recording head.

Recording Medium

The above-described novel compound of this invention can be contained in a recording medium, for example, a recording medium used in ink-jet recording. By using such a recording medium for ink-jet recording, ink-jet recorded articles of high quality can be obtained. One method to make the recording medium contain the novel compound of this invention is to coat the recording medium with the compound as a water-soluble binder. After recording is performed on such a recording medium with an aqueous ink, the water-soluble groups of the compound are removed by retro-Diels-Alder reaction to make the surface of the recording medium hydrophobic. According to this operation, the degree to which the retro-Diels-Alder reaction progresses can be adjusted by controlling the energy application to the recording medium, so that the degree of hydrophobicity of the recording medium can be adjusted. Thus, satisfactory fixing and little bleeding of aqueous ink provided to the recording medium can be both accomplished at a higher level.

In this embodiment, the recording medium on which recording is carried out is not specifically limited, and appropriately selected from the recording media applicable to the ink-jet recording methods using aqueous ink. Such recording media include, for example, information transmitting sheets such as paper and film, fibers and leather. As to the information transmitting sheets, those having treated surface, in more particular, those having an ink-receiving layer provided on a base material, are preferable. The ink-receiving layer is provided by impregnating or coating with a cationic polymer, or by coating with porous silica, alumina sol or special ceramic together with a hydrophilic polymer such as polyvinyl alcohol. It goes without saying that plain paper can be used as a recording medium.

Additives etc.

Various additives can be added to ink, liquid compositions, or recording medium. The examples of such additives include, not limited to, anti-oxidants represented by hindered amine and hindered phenol, and ultraviolet absorbers represented by salicylic-acid compounds and benzotriazole compounds. These additives are generally water-insoluble, and to be added in ink-jet recording ink or ink-jet recording medium, water-soluble substitutes (e.g. hydroxyl group, carboxyl group and sulfonic acid group) are usually introduced into the additives. In such a case, however, migration (flowing-out) of the additives may occur under the influence of moisture, for example, under a high humidity, lowering the effects of the additives. If the molecular weight of the additive is increased to prevent migration, the solubility of the additive will be lowered to affect the expected effect of the additive. Accordingly, use of the mechanism according to this invention, i.e., elimination of soluble groups and structure conversion of a compound may control the solubility of the additives to prevent migration; as a result, the good solubility and migration prevention can be both achieved. For this purpose, it is preferable to design the size, polarity and position of the groups to be removed from the precursor and to be remained on the product from the precursor.

Environmental History Detecting Method

As already described, one means for inducing retro-Diels-Alder reaction of the compound of the invention is heating. Thus, this nature of the compounds can be used as means for detecting heat history of an article. Specifically, it is possible to design that the color of a compound will change before and after retro-Diels-Alder reaction utilizing the structural change of the compound, in particular, by construction of π conjugated system. Utilizing such change in color, it is possible to detect whether or not heat at a certain level or higher has been applied to an article. For example, the compounds of this invention having a porphyrin skeleton or tetraazaporphyrin skeleton change color when they are heated to a temperature equal to or higher than that will induce retro-Diels-Alder reaction. Although such a threshold temperature may differ depending on the compounds designed, with the novel compounds described above, color change is observed with heating at 120° C. or higher. Accordingly, the heat history of an article can be appreciated by attaching a compound of this invention to the article and observing whether or not the color of the compound has changed due to retro-Diels-Alder reaction.

Method for Purifying Compounds

Compounds can be purified using the technique according to this invention. For example, various organic functional materials having extended π electrons are considered useful. However, such compounds, for example, tetraazaporphyrin compounds (e.g. phthalocyanine) are hard to dissolve in solvents due to the molecular stacking, therefore, hard to remove impurities contained among the molecules for purification. However, using the technique of the present invention, it is possible to introduce bulky bicyclooctadiene skeleton having hydrophilic groups to ensure the solubility in a aqueous solvent in the synthesis of phthalocyanine, to carry out purification by conventional procedure such as filtration or extraction to remove impurities; and then remove substituted ethylene group by retro-Diels-Alder reaction to allow extension of π electron system. Thus, a desired compound, a phthalocyanine compound of high purity can be easily obtained.

Pattern Forming Method

Retro-Diels-Alder reaction of the compounds of this invention enables film formation of a compound having organic semiconductor properties. It is generally known that anthracene, tetracene, polythiophene, porphyrin, and tetraazaporphyrin (e.g. phthalocyanine) compounds have organic semiconductor properties. However, many of these compounds are hard to dissolve in solvents because its π electron system has an expanded plane structure, as a result, a film of such a compound has been formed only by deposition. However, film formation by deposition has disadvantages that it is a batch method and has various limitation to the filming conditions, and uniform film formation in a a large area is difficult and, moreover, it is costly.

The use of the technique according to this invention permits the compounds of, for example, anthracene, tetracene, polythiophene, porphyrin, tetraazaporphyrin (e.g. phthalocyanine) to have solubility in solvents, and film can be formed from a solution of such a compound by cast-film process. After the film formation, ethylene group is removed by retro-Diels-Alder reaction from the compound of the film and the π electron system in the molecule are expanded to obtain organic semiconductor film of the desired compound. The film forming processes applicable include, for example, cast-film process such as spin coating or dip coating. In addition, with compounds such as anthracene, tetracene, polythiophene, porphyrin, and tetraazaporphyrin (e.g. phthalocyanine) compounds, screen printing and ink-jet printing are also applicable. These film forming processes allow formation of film of large area at lower cost. If printing by ink-jet method is employed, ink can be provided selectively at a desired position on a recording medium with a high accuracy, and a highly accurate pattern of an organic semiconductor can be generated on the recording medium by retro-Diels-Alder reaction on the recording medium that makes the compound insoluble in the solvent. Since the solubility of these compounds in solvents can be lowered only after the compounds are provided on the base material (recording medium), the behavior of the solvent on the recording medium and that of organic semiconductor material (herein mean the compounds, for example, anthracene, tetracene, polythiophene, porphyrin, tetraazaporphyrin (e.g. phthalocyanine)) can be independent of each other. Specifically, even when the solvent spreads on a base material in disorder, the organic semiconductor material that becomes insoluble to the solvent would not spread with the solvent. This also contributes to the formation of patterns of higher accuracy.

EXAMPLES

In the following the advantages of this invention will be further clarified by means of the examples based on this invention; however, it should be understood that these examples are shown for illustrative purposes only and are not intended to limit this invention.

Hereinafter the following abbreviations will be used.
THF: tetrahydrofuran
DBU: 1,8-diazabicyclo-[5,4,0]undecene-7

Example 1

Synthesis of Porphyrin Compounds

A porphyrin compound of this invention having hydroxyl groups eliminable by retro-Diels-Alder reaction was synthesized as a coloring material in accordance with the scheme shown in FIG. 1.

1.1. Synthesis of Compound 2

First a 20% solution of 3,5-cyclohexadien-1,2-diol (compound 1) in ethyl acetate (25 ml) was prepared as a raw material, the solvent was concentrated under reduced pressure, and acetone (30 ml), 2,2-dimethoxypropane (69 ml) and a trace amount of p-toluensulfonic acid were added, followed by stirring at room temperature for 4 hours. Then a 10% aqueous solution of sodium hydroxide (30 ml) and saturated brine (30 ml) were added and stirred to stop the reaction, the reaction solution was extracted with diethyl ether (3×30 ml), the organic layer was washed with saturated brine (3×30 ml), dried with sodium sulfate anhydride, and concentrated under reduced pressure to obtain a compound 2,which is the compound 1 with its hydroxyl groups protected, in a yield of 8.33 g.

1.2. Synthesis of Compound 3

The compound 2 (158 mg, 1.04 mmol) and 2-nitro-1-(phenylsulfonyl)ethylene (230 mg, 1.08 mmol) were put into a reactor, toluene (2.00 ml) was added, followed by stirring at 90° C. for 3 hours. After the completion of the reaction, the reaction solution was concentrated under reduced pressure and column chromatographed (20 to 30% by volume ethyl acetate/hexane), and the fractions of Rf 0.24 (20% by volume ethyl acetate/hexane) and Rf.0.18 (20% by volume ethyl acetate/hexane) were concentrated. These concentrated fractions were recrystallized to obtain compounds 3a and 3b in yields of 124 mg (0.339 mmol, 32.6% by mass) and 62 mg (0.17 mmol, 16.3% by mass), respectively.

mp 151.9-152.6° C. $^1$H NMR (solvent: $CDCl_3$) unit: δppm 7.87 (m, 2H), 7.71 (m, 1H), 7. 59 (m, 2H), 6.16 (m, 2H), 4.81 (dd, J=5.6, 2.4 Hz, 1H), 4.33 (dd, J=6.8, 2.9 Hz, 1H), 4.19 (dd, J=6.8, 2.9 Hz, 1H), 4.04 (dd, J=5.6, 1.5 Hz, 1H), 3.70 (m, 1H), 3.48 (m, 1H) 1.28 (s, 3H), 1.22 (s, 3H) IR (KBr)/cm$^{-1}$ 2981 w, 1552 s, 1313 s, 1151 s, 1056 s, 727.0 m, 601.7 m.

1.3. Synthesis of Compound 4

365 mg (1 mmol) of compounds 3a, 3b (2,2-dimethyl-8-nitro-9-phenylsulfonyl-3a,4,7,7a-tetrahydro-4,7-ethano-1,3-benzodioxole) were put into a reactor, purged with nitrogen gas and dissolved in dry THF (5.00 ml), and the reactor was immersed in an ice bath. After dry ethyl isocyanoacetate (0.110 ml, 1.00 mmol) was added, DBU having been distilled with calcium hydride (0.370 ml, 2.50 mmol) was added dropwise over 5 minutes, and the ice bath was removed, followed by stirring at room temperature for 17 hours. After the completion of the reaction, 2% hydrochloric acid (10.0 ml) was added, and the reaction solution was extracted with ethyl acetate (3 ×20.0 ml ). The organic layer was washed with saturated brine, dried with sodium sulfate anhydride, concentrated under reduced pressure and silica gel column chromatographed (5% by volume ethyl acetate/chloroform), and the fraction Rf 0.41 (5% by volume ethyl acetate/chloroform) was concentrated and recrystallized to obtain a compound 4 in a yield of 283 mg (97.8 mmol, 97.8% by weight).

mp 114.9-146.3° C. $^1$H NMR (solvent: CDCl$_3$, unit: δppm) 8.58 (Br, 1H), 6.68 (d, J=2.4 Hz, 1H), 6.50 (m, 2H), 4.56 (m, 1H) 4.34 (m, 2H), 4.32 (q, J=7.0 Hz, 2H), 4.06 (m, 1H), 1.42 (s, 3H), 1.38 (t, J=7.0 Hz, 3H), 1. 30 (s, 3H) IR (KBr)/cm$^{-1}$ 3345 s, 2892 w, 1681 s, 1297 m, 1141 s, 1039 s.

1.4. Synthesis of Compound 5

The compound 4 (289 mg, 1.00 mmol) was put into a reactor purged with nitrogen gas and dissolved in dry THF (5.00 ml), and the reactor was immersed in an ice bath. Aluminium lithium hydride (114 mg, 3.00 mmol) was added and the ice bath was removed, followed by stirring at room temperature for one hour. After the completion of the reduction, saturated brine (20.0 ml) was added, the insolubles were Celite filtrated, the reaction solution was extracted with chloroform (3×100 ml) and dried with sodium sulfate hydride p-toluenesulfonic acid (80.0 mg) was added to the solution, followed by stirring for one day. Further, chloranil (223 mg, 0.907 mmol) was added to the solution, followed by stirring for one day. After the completion of the reaction, the reaction solution was washed with an 1% aqueous solution of sodium thiosulfate (50.0 ml) and saturated brine (50.0 ml), respectively, dried with sodium sulfate anhydride, concentrated under reduced pressure, and column chromatographed and recrystallized to obtain a compound 5 (in a yield of 39.8% by weight).

1.5. Synthesis of Compound 6

The compound 5 and copper acetate were put into a reactor, dissolved in chloroform (30 ml)—methanol (3 ml), followed by stirring at room temperature for 3 hours. After the completion of the reaction, the reaction solution was washed with water (100 ml×2) and saturated brine (40 ml), successively, dried with sodium sulfate anhydride, concentrated under reduced pressure, and recrystallized from chloroform—methanol to obtain a reddish purple crystal (compound 6).

1.6. Synthesis of Compound 7

The resultant compound 5 was hydrolyzed in the presence of acid to be subjected to deprotecting, to obtain an intended water-soluble compound 7.

Example 2 and Reference Example

Preparation of Ink-Jet Recording Ink and Image Recording

Two types of ink-jet recording ink (aqueous ink) were prepared: one using the water-soluble compound 7,which was obtained in Example 1 and desalted through an ultrafiltration membrane; and the other, as a reference example, using phthalocyanine pigment (C.I. Direct Blue 199).

| | |
|---|---|
| 1) Desalted water-soluble compound 7 or C.I. Direct Blue 199 | 5.0 parts |
| 2) Glycerol | 5.0 parts |
| 3) Urea | 5.0 parts |
| 4) Ethylene glycol | 5.0 parts |
| 5) Water | 80.0 parts |
| Total | 100.0 parts |

Reddish purple color square patches of 1 cm×1 cm were printed on a recording medium (trade name: PR-101; manufactured by Canon Inc.) using the above two types of ink on an ink-jet printer, trade name: BJ-F 870; manufactured by Canon Inc. The color patches of Example 2 were heat treated at 120° C. for 1 minute for retro-Diels-Alder reaction of the compound 7 and converted into cyan color patch. The resultant color patches of Example 2 and Reference Example were tested for their light-fastness, gas-fastness, water-fastness and moisture-fastness.

Light-Fastness

Light-exposure-fastness test was conducted with a xenone fade meter in accordance with the following test conditions. This was to test fastness of an image mimicking sunlight entering through a window in a room.
Test Conditions:
Irradiation Intensity: 70 Kl×testing duration 520 hours
Temperature/humidity conditions in a testing vessel: 24° C., 60% RH
Filter: soda lime (outer), borosilicate (inner)
The light-fastness was evaluated as follows:
A: Density remaining rate of 90% or more
B: Density remaining rate of 89 to 80%
C: Density remaining rate of 79% or less Gas-Fastness Gas-exposure-fastness test was conducted with a gas corrosion tester under the following test conditions (ANSI/ISA-S71.04-1985). This was to test fastness of an image assuming the effects of various gases in a room.
Test Conditions:
Exposing gas composition: H$_2$S: δppb, SO$_2$: 300 ppb, NO$_2$: 1250 ppb, Cl$_2$: 10 ppb, O$_3$: 1200 ppb
Testing duration: 72 hours, Temperature/humidity conditions in a testing vessel: 24° C., 60% RH
The gas-fastness was evaluated as follows:
A: Density remaining rate of 90% or more
B: Density remaining rate of 89 to 80%
C: Density remaining rate of 79% or less Water-Fastness The obtained recorded article was immersed in city water for 5 minutes, drawn up from the water and dried, and its change in density before and after the test was determined.
A: Density reduction rate of 1% or less
B: Density reduction rate of 2 to 4%
C: Density reduction rate of 5% or more Humidity-Fastness The obtained recorded article was stored in a thermohydrostat vessel at 30° C., 80% RH for 1 week, drawn from the vessel and dried, and its change in density before and after the test was determined.
A: Density reduction rate of 1% or less
B: Density reduction ate of 2 to 4%
C: Density reduction rate of 5% or more
The summarized results of the above tests for the compound 7 before and after conversion by heating and the ink of the reference example (Direct Blue 199) are shown in Table 1.

TABLE 1

| | Example 2 | | Reference Example DBL-199 |
| --- | --- | --- | --- |
| | Printed article before conversion by heating | Printed article after conversion by heating | |
| Light-fastness | B | A | A |
| Gas-fastness | C | A | C |
| Water-fastness | C | A | C |
| Humidity-fastness | B | A | B |

As described above, the use of the recording method according to this invention permits ink to change from a solvent-soluble system to a solvent-insoluble system on a recording medium. By changing (lowering) the solubility of the coloring material on a recording medium, self-cohesion of the coloring materials is induced, endowing superior fastness to recorded images. Further, the ink of this invention requires no addition of polymer dispersing agent, unlike in the case of the conventional ink. Thus, according to this invention, advantages of the conventional dye ink and the conventional pigment ink are both given.

Example 3

Synthesis of Tetraazaporphyrin Compound

Figure 2:
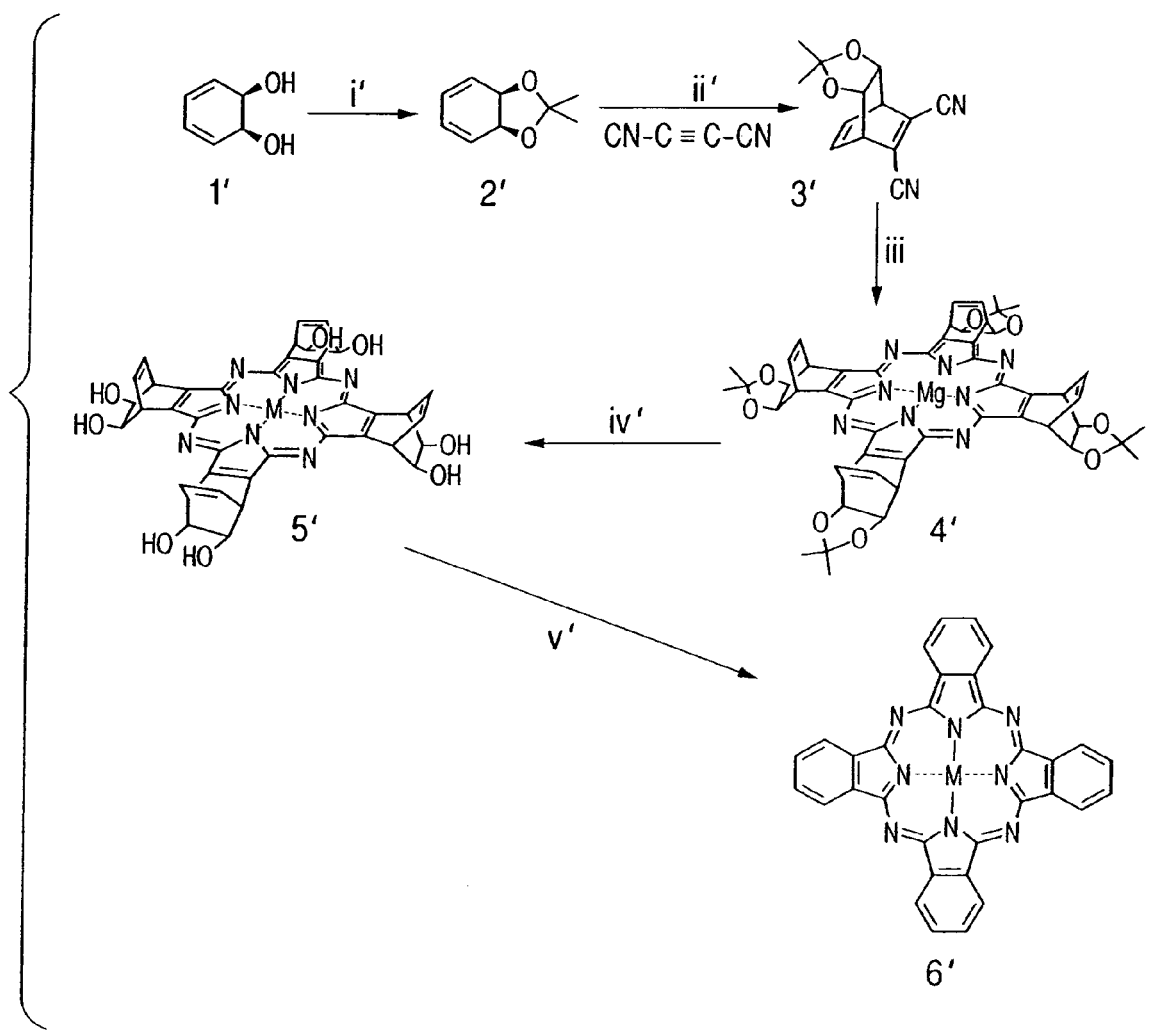
FIG. 2 is a scheme of a method for synthesizing a tetraazaporphyrin compound according to this invention.

A compound of this invention having a tetraazaporphyrin skeleton was synthesized in accordance with the scheme shown in FIG. 2.

3.1. Synthesis of Compound 2'

First, a 20% solution of 3,5-cyclohexadien-1,2-diol (compound 1') in ethyl acetate (25 ml) was prepared as a raw material, the solvent was concentrated under reduced pressure, and acetone (30 ml), 2,2-dimethoxypropane (69 ml) and a trace amount of p-toluensulfonic acid were added, followed by stirring at room temperature for 4 hours. Then a 10% aqueous solution of sodium hydroxide (30 ml) and saturated brine (30 ml) were added and stirred to stop the reaction, the reaction solution was extracted with diethyl ether (3 ×30 ml), the organic layer was washed with saturated brine (3 ×30 ml), dried with sodium sulfate anhydride, and concentrated under reduced pressure to obtain a compound 2,which is the compound 1' with its hydroxyl groups protected, in a yield of 8.33 g.

3.2. Synthesis of Compound 3'

The compound 2' (158 mg) and dicyanoacetylene (230 mg) were put into a reactor, toluene (2.00 ml) was added, followed by stirring at 90° C. for 3 hours. After the completion of the reaction, the reaction solution was concentrated under reduced pressure and column chromatographed (20-30% by volume ethyl acetate/hexane), and the fractions of Rf 0.24 (20% by volume ethyl acetate/hexane) and Rf 0.18 (20% by volume ethyl acetate/hexane) were concentrated. These concentrated fractions were recrystallized to obtain a compound 3' in yields of 184 mg.

mp: 151.9-152.6° C. $^1$HNMR (solvent: CDCl$_3$ unit: δppm 7.87 (m, 2H), 7.71 (m, 1H), 7. 59 (m, 2H), 6.16 (m, 2H), 4.81 (dd, J=5.6, 2.4 Hz, 1H), 4.33 (dd, J=6.8, 2.9 Hz, 1H), 4.19 (dd, J=6.8, 2.9 Hz, 1H), 4.04 (dd, J=5.6, 1.5 Hz, 1H), 3.70 (m, 1H), 3.48 (m, 1H) 1.28 (s, 3H), 1.22 (s, 3H) IR (KBr)/cm$^{-1}$ 2981 w, 1552 s, 1313 s, 1151 s, 1056 s, 727.0 m, 601.7 m.

3.3. Synthesis of Compound 4'

The compound 3 (365 mg) was put into a reactor purged with nitrogen gas and dissolved in dry THF (5.00 ml). Then a solution of n-butoxymagnesium in n-butanol was added, stirred while heating at 150° C., to subject the compound to tetrameric cyclization and metal complex. After the completion of the reaction, the reaction solution was extracted with ethyl acetate (3×2.0.0 ml). The organic layer was washed with saturated brine, dried with sodium sulfate anhydride, concentrated under reduced pressure and silica gel column chromatographed (5% by. volume ethyl acetate/chloroform), and the fraction Rf 0.41 (5% by volume ethyl acetate/ chloroform) was concentrated and recrystallized to obtain a compound 4' in a yield of 283 mg.

mp 114.9-146.3° C. 1H NMR (solvent:CDCl$_3$ unit: δppm) 8.58 (Br, 1H), 6.68 (d, J=2. 4 Hz, 1H), 6.50 (m, 2H), 4.56 (m, 1H) 4.34 (m, 2H), 4.32 (q, J=7.0 Hz, 2H), 4.06 (m, 1H) 1.42 (s, 3H), 1.38 (t, J=7.0 Hz, 3H), 1.30 (s, 3H) IR (KBr)/cm$^{-1}$ 3345 s, 2892 w, 1681 s, 1297 m, 1141 s, 1039 s.

3.4. Synthesis of Compound 5'

The compound 4' (289 mg) was put into a reactor purged with nitrogen gas and dissolved in THF (5.00 ml). 1 N hydrochloric acid (114 mg) was added and stirred at room temperature for 1 hour. After the completion of the reaction, saturated brine (20.0 ml) was added, the reaction solution was washed with 1% aqueous solution of sodium thiosulfate (50.0 ml) and saturated brine (50.0 ml), respectively, dried with sodium sulfate anhydride, concentrated under reduced pressure, and column chromatographed and recrysallized, to obtain water-soluble phthalocyanine compound 5' with its hydroxyl groups deblocked (in a yield of 39.8%).

According to this invention, two different properties: excellent solubility in ink and fast solid-liquid separation after provided on a recording medium, are satisfied at a considerably high level, such compatibility has been considered difficult in the prior art.

This invention also enables the change in properties of a compound, for example, conversion from a solvent-soluble system before patterning to a solvent-insoluble system after patterning. It enables dramatic improvement in image fastness.

What is claimed is:

1. A method for forming an organic semiconductor film, comprising the steps of:

applying onto a base material at least a bicyclo compound having a structure represented by formula

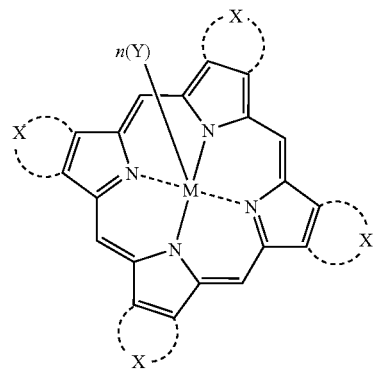

-continued

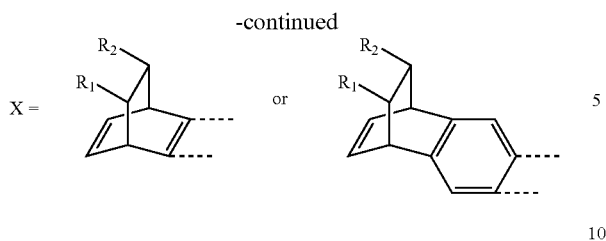

wherein M represents an element selected from Zn, Cu, Fe, Mg, Al, Ga, Ti and Sn; Y represents a halogen atom, an oxygen atom or a hydroxyl group; n is an integer of 0 to 2; and R1 and R2 represent a polar group containing at least any one of an oxygen atom, a nitrogen atom and a sulfur atom, or an alkyl group; and inducing retro-Diels-Alder reaction in the bicyclo compound.

2. The method according to claim 1, wherein the polar group is an alkoxy group.

3. The method according to claim 1, wherein the retro-Diels-Alder reaction is induced by heating and light irradiation.

4. A method for forming a pattern of an organic semiconductor film, comprising the steps of:

applying a solution containing at least a bicyclo compound to a desired position on a base material; and inducing a retro-Diels-Alder reaction in the bicyclo compound at a selected position on the base material to thereby form a pattern of an organic semiconductor film having a size of nanometers at the selected position, wherein the bicyclo compound has a structure represented by formula

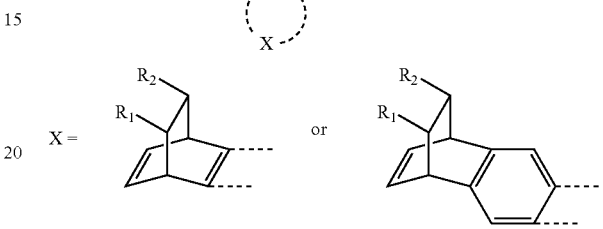

wherein M represents an element selected from Zn, Cu, Fe, Mg, Al, Ga, Ti and Sn; Y represents a halogen atom, an oxygen atom or a hydroxyl group; n is an integer of 0 to 2; and $R_1$ and $R_2$ represent a polar group containing at least any one of an oxygen atom, a nitrogen atom and a sulfur atom, or an alkyl group.

5. The method according to claim 4, wherein the polar group is an alkoxy group.

* * * * *

UNITED STATES PATENT AND TRADEMARK OFFICE
CERTIFICATE OF CORRECTION

| | |
|---|---|
| PATENT NO. | : 7,315,043 B2 |
| APPLICATION NO. | : 11/500996 |
| DATED | : January 1, 2008 |
| INVENTOR(S) | : Takayuki Ishikawa et al. |

It is certified that error appears in the above-identified patent and that said Letters Patent is hereby corrected as shown below:

ON THE TITLE PAGE, Item (56), References Cited,
OTHER PUBLICATIONS
Line 11 (for "Noboru Ono, et al."), "Porphyrin" should read --Porphyrins--.

Line 21 (for "Papies et al."), "Letters" should read --Letters 21--.

Line 45, "March 21, 2000, p. 1294" should read --March 21, 2001, p. 1294--.

Line 49, --Proceedings of the 78th Annual Meeting of the Chemical Society of Japan, 17 March 2000, p. 712, ID 1 44.-- should be inserted.

Line 50, --Proceedings of the 79th Annual Meeting of the Chemical Society of Japan, 21 March 2001, p. 1287, 3 H6 02.-- should be inserted.

COLUMN 6
Line 3, "according" should read --according to that--.
Line 51, "sovlent-phlic" should read --solvent-philic--.
Line 55, "or a" should read --or an--.

COLUMN 11
Line 66, "nitrosulfoyl" should read --nitrosulfonyl--.

COLUMN 13
Line 41, "is" should read --are--.

COLUMN 16
Line 63, "of of" should read --of--.

COLUMN 17
Line 9, "affected" should read --to be affected--.
Line 18, "used-for" should read --used for--.

COLUMN 20
Line 12, "not" should read --but are not--.

COLUMN 21
Line 4, "a" should read --an--.

COLUMN 22
Line 43, "$^1$H" should start a new paragraph.

CERTIFICATE OF CORRECTION (continued)
U.S. Pat. No. 7,315,043 B2

COLUMN 23
Line 4, "$^1$H" should start a new paragraph.
Line 53, "7,which" should read --7, which--.

COLUMN 24
Line 35, "δppb" should read --50 ppb--.
Line 61, "ate" should read --rate--.

COLUMN 25
Line 46, "2,which" should read --2, which--.
Line 61, "$^1$H NMR" should begin a new paragraph and read --$^1$H NMR--.

COLUMN 26
Line 11, "by." should read --by--.
Line 15, "1H" should begin a new paragraph and read --$^1$H--.
Line 31, "recrysallized" should read --recrystallized--.

COLUMN 27
Line 15, "R1 and R2" should read --$R_1$ and $R_2$--.

Signed and Sealed this

Nineteenth Day of January, 2010

David J. Kappos
*Director of the United States Patent and Trademark Office*